United States Patent [19]
Goyne

[11] 4,191,351
[45] Mar. 4, 1980

[54] MOUNTING FLUID FLOW APPARATUS

[75] Inventor: Thomas E. Goyne, Denver, Colo.

[73] Assignee: Cobe Laboratories, Inc., Lakewood, Colo.

[21] Appl. No.: 844,144

[22] Filed: Oct. 20, 1977

[51] Int. Cl.² .......................................... F16M 13/00
[52] U.S. Cl. .......................................... 248/311.1 R
[58] Field of Search ............... 248/130, 133, 137, 140, 248/142, 311.1 R, 311.3; 221/188; 222/166

[56] References Cited

U.S. PATENT DOCUMENTS

| | | | |
|---|---|---|---|
| 1,233,091 | 7/1917 | Maier | 248/142 |
| 1,326,077 | 12/1919 | Manahan | 248/142 |
| 2,926,879 | 3/1960 | Dietrich | 248/311.1 |
| 3,060,934 | 10/1962 | Claff et al. | 128/214 |
| 3,332,746 | 7/1967 | Claff et al. | 23/253.5 |
| 3,734,439 | 5/1973 | Wintz | 248/311.1 X |
| 4,019,708 | 4/1977 | Croup | 248/137 |

FOREIGN PATENT DOCUMENTS 636878 10/1936 Fed. Rep. of Germany .......... 248/130

*Primary Examiner*—William H. Schultz

[57] ABSTRACT

A mount for a fluid flow transfer apparatus for facilitating degassing of the apparatus comprises a pair of trunnions for cooperating with a pair of stub shafts on opposite sides of the fluid flow transfer apparatus, to permit rotation of the apparatus, and a selectively disengageable latch spaced radially from the axis of rotation of the trunnions and shafts, to secure the apparatus against rotation once the apparatus is placed in either an operational position or an inverted degassing position.

15 Claims, 5 Drawing Figures

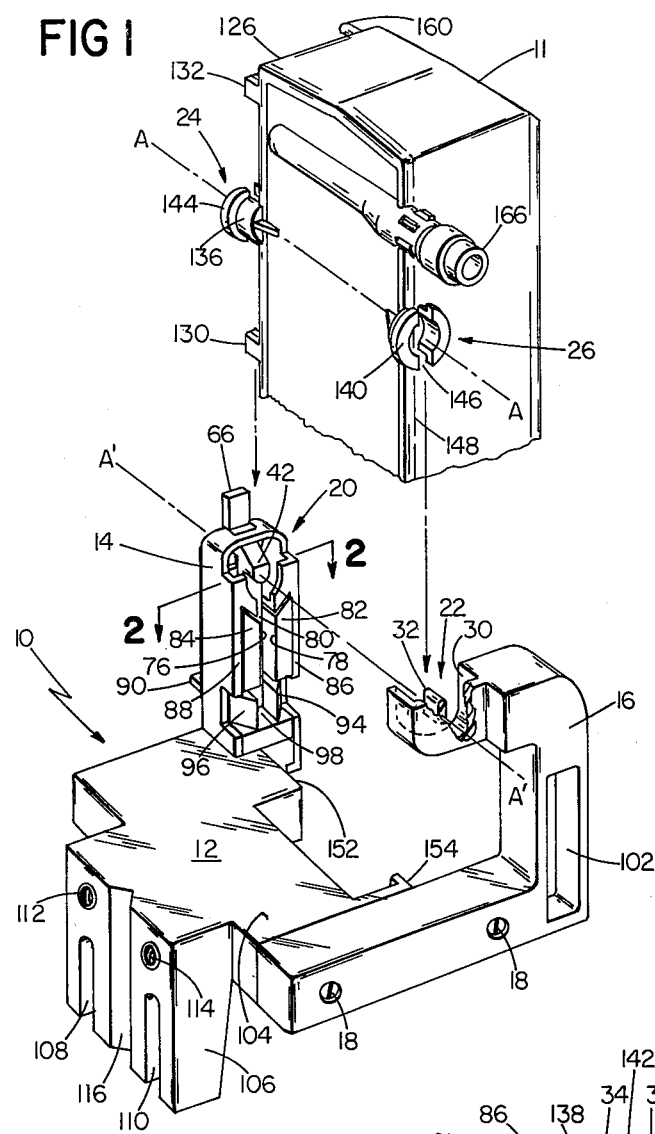
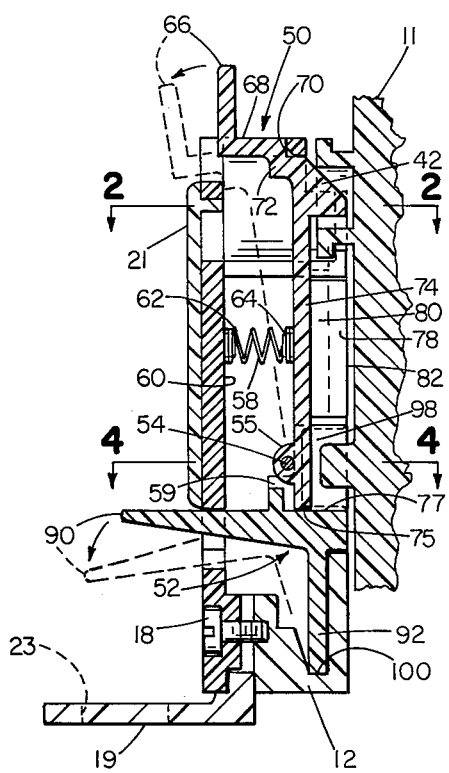
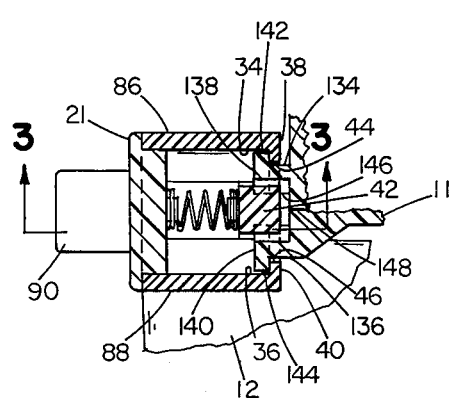
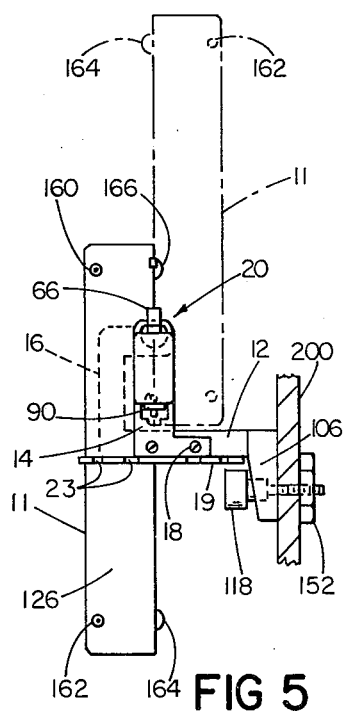

MOUNTING FLUID FLOW APPARATUS

FIELD OF THE INVENTION

The invention relates to a mount for a fluid flow transfer apparatus.

BACKGROUND OF THE INVENTION

In fluid flow transfer apparatus, such as hemodialyzers or artificial kidneys, it is necessary, at times, to expel air initially present in fluid circuits in the apparatus, such air expulsion being referred to as degassing. This need is acute when fluid travels downward through the apparatus in its normal mode of operation, for then initially entrapped air rises against the direction of fluid flow so that escape of the air is retarded.

The known method for degassing downwardly flowing fluid circuits is to turn the apparatus upside down until the initially entrapped air in the circuit has exited by going up with the now upwardly flowing fluid. This can be done by simply taking the apparatus out of its mount and manually rotating it, but this carries the risk of dropping the device, a serious matter when the apparatus is a hemodialyzer. Thus, it would be desirable to have a mount for the apparatus that permits rotation of the apparatus easily, reliably, and quickly into an upside down degassing position and locking therein and reliable return to a normal vertical operating position and locking therein, thus making removal of the apparatus for rotation unnecessary.

Rotatable mounts are known, but the need remains for a mount that securely holds the fluid flow apparatus in each desired position, that does not require careful adjustment to change position, and that facilitates insertion and removal of the apparatus from the mount.

A mount manufactured by Cordis Dow Corporation for a cylindrical hemodialyzer comprises a semicircular clamp into which the hemodialyzer is snapped and a generally C-shaped clamp which fits around an upright mounting pole and to which the semicircular clamp is rotatably connected back-to-back. A detent comprising a shaft extending horizontally from the semicircular clamp and having recesses circumferentially spaced apart at 30° to cooperate with a spring-biased ball on the C-clamp permits holding the hemodialyzer in rotational positions 30° apart. There are no means other than the detent, which is located at the site of rotation, for securing the hemodialyzer in a selected position.

Claff et al. U.S. Pat. No. 3,332,746 shows a mount having trunnions cooperating with a pair of shafts on opposite transverse surfaces of an oxygenator held in a vertical position and said to be tiltable in any direction. The mount has a lower horizontal bar, partially concealed in the drawing, which appears to support the oxygenator in a vertical position.

Claff et al. U.S. Pat. No. 3,060,934 shows a clamp for selectively locking an oxygenator in a desired tilted position.

SUMMARY OF THE INVENTION

I have invented a mount that provides the desired rotation and locking and is easily operated. It has a pair of trunnions for cooperating with a pair of stub shafts on opposite sides of a fluid flow transfer apparatus to permit rotation of the apparatus, and has a selectively disengageable first latch spaced radially from the axis of rotation of the trunnions and shafts for securing the apparatus against rotation once the apparatus is placed in either an operational position or an inverted degassing position.

In preferred embodiments the selectively disengageable first latch is adapted to cooperate with either of a pair of protuberances equally spaced above and below one stub shaft on one side of the apparatus, and there is a second selectively disengageable latch for preventing removal of the fluid flow transfer apparatus from the mount. This second latch has a projection extending axially inside the hollow interior of one stub shaft to maintain axial alignment of the trunnion connection. Further, the projection is tapered so as to snap past one of the protuberances and the stub shaft, thereby permitting drop-in insertion of the apparatus in the mount. The first latch is also provided with sloping surfaces and is spring biased to allow one of the protuberances to snap into the latch when the apparatus enters either the operating position or the inverted degassing position.

In addition to having the advantage of combining easy but sure rotation of a fluid flow transfer apparatus to and from predetermined positions with secure locking in each of the positions, the mount makes installation and removal of the apparatus a simple matter; thus installation in the preferred embodiment is accomplished by downward insertion of the apparatus into the mount. Latch snap action during insertion and during rotation into either the operational or degassing position provides audible feedback that the desired movement has been achieved. And all of these operating conveniences are obtained with a simple and sturdy construction, the mount being preferably principally composed of a few molded plastic parts.

DESCRIPTION OF THE PREFERRED EMBODIMENT

The structure and operation of the preferred embodiment of the invention follow:

Structure

The drawings show the preferred embodiment, which is then described.

Drawings

FIG. 1 is an isometric view of said embodiment, showing a hemodialyzer (only top half shown) being inserted into the operating position in said embodiment;

FIG. 2 is a horizontal sectional view taken through 2—2 of FIG. 1 (with the hemodialyzer inserted);

FIG. 3 is a vertical sectional view taken through 3—3 of FIG. 2 showing the upper and lower latches connected to a hemodialyzer (broken away);

FIG. 4 is a horizontal sectional view taken through 4—4 of FIG. 3, showing the lower latch engaging a hemodialyzer protuberance; and FIG. 5 is an elevation view of said embodiment installed on a dialysis machine with the hemodialyzer in its operating position, the degassing position being shown in broken lines.

Description

Turning to FIG. 1, there is shown a hemodialyzer degassing mount, indicated generally at 10, into which hemodialyzer 11 (shown partially), such as the parallel plate hemodialyzer manufactured by Cobe Laboratories, Inc., of Lakewood, Colo., is about to be inserted. The mount has base 12 from which extend front arm 14

(rearmost arm in FIG. 1) and rear arm 16, the arms being secured to the base by screws 18. A logo plate 21 (shown in FIG. 3) is attached to the front side (not seen in FIG. 1) of arm 14.

At the end of each arm there are coaxial trunnions 20, 22 cooperating with coaxial (about axis A—A) stub shafts 24, 26 molded on the hemodialyzer to form a rotatable connection about axis A'—A' between the mount and hemodialyzer. Trunnion 22 on rear arm 16 includes a U-shaped bearing surface 30 surrounding a vertical rectangular projection 32, which is centrally located with relation to the circular portion of the bearing surface. On front arm 14 trunnion 20 includes co-cylindrical bearing surfaces 34, 36 (FIG. 2); lips 38, 40, which are positioned outside of surfaces 34, 36; further co-cylindrical bearing surfaces 44, 46 on the lips; and centrally located, semicylindrical, tapering projection 42.

Inside front arm 14 is a latch mechanism (FIG. 3) having molded plastic upper and lower latch elements 50, 52, which pivot relative to each other. A coil spring 58, held at each end by cylindrical projections 62, 64, is located between upper element 50 and the inside back surface 60 of the arm. At its upper end upper latch element 50 has dialyzer-removal tab 66 with horizontal extension 68 fitting closely within slot 70 in the top of arm 14. And below tab 66 and portion 68, step 72 connects horizontal portion 68 with semicylindrical, tapering projection 42, and vertical leg 74 extends from projection 42 downward, its bottom surface 75 resting on horizontal surface 77 of lower latch element 52. On either side of vertical leg 74, walls 76, 78 form latch channel 80, having the width of projection 42. The walls have top surfaces 82, 84 extending perpendicularly outwardly from the channel and fitting closely within side walls 86, 88 of the arm, thus preventing lateral motion of upper latch element 50. Near the bottom of vertical leg 74, steel dowel 54 is held tightly by semicylindrical sleeve 55 protruding from the interior side of the leg.

The two protruding ends of dowel 54 (FIG. 4) bear against flat faces 56 of lower latch element 52, and ends 57 of sleeve 55 bear against shoulders 59 of the lower element, preventing relative lateral motion of the two latch elements.

Lower latch element 52 includes a horizontally projecting dialyzer-rotation tab 90; a vertical leg 92; shoulders 59 bearing against sleeve 55 (FIG. 4); flat faces 56 which bear against the two ends of dowel pin 54; a pair of opposed walls 94, 96, which have sloping outer surfaces and which form latching channel 98, in which the bottom end of the upper latch element fits; and horizontal surface 77 on which bottom surface 75 of the upper element rests. Vertical leg 92 rests within tapered well 100 in base 12.

On the side opposite the arms, base 12 has a bracket 106 having slots 108, 110; threaded inserts 112, 114; and V-shape groove 116, all for mounting purposes, as explained more fully hereinafter. Counterclockwise rotation is prevented by stop surfaces 152, 154 and base 12.

Shelf 19 (FIGS. 3 and 5, not shown in FIG. 1) having two holes 23 therein to hold two drip chambers is secured to base 12 beneath front arm 14.

On side 126 of hemodialyzer 11 there are molded two protuberances 130, 132. Each stub shaft has co-cylindrical inner bearing surfaces 134, 136; annular lips 138, 140; and further co-cylindrical outer bearing surfaces 142, 144, associated surfaces and lips being separated by central slot 146. Protuberances 130, 132 are equally spaced above and below stub shaft 24. The parting line 148 between interfitting portions of the hemodialyzer casing passes centrally through both the protuberances and slot 146.

The arms and base are molded from glass-filled polycarbonate plastic and have hollowed portions 102 (some not shown) for material and weight reduction purposes. And underneath horizontal surface 104 of base 12 there are molded cross members (not shown) to strengthen and stiffen the base.

Operation

As depicted in FIG. 5, the degassing mount is installed on a dialysis unit 200 (shown schematically). Thumb screws 118 pass through slots 108, 110 and matching holes drilled in the side of the dialysis unit and are threadedly secured to backing plate 152, inside the unit. Alternatively, the degassing mount can be pole mounted by clamping an IV pole between the V-shape grooves in the base bracket 106 and a pole bracket (not shown), using the thumb screws threaded into inserts 112, 114 for tightening.

Hemodialyzer 11 is installed in the degassing mount by simply inserting it downwardly into the mount while orienting the protuberances and stub shafts with the latch channels 80, 98 and trunnions 20, 22, as suggested by the arrows in FIG. 1. Projection 42 deflects to allow protuberance 130 to pass into latch channel 80, which guides the protuberance down into latch channel 98. Installation is completed by projection 42 snapping by means of its tapered surface into the center of stub shaft 24 and on the other side projection 32 being positioned in the center of stub shaft 26, the projection having passed through channel 146 in the stub shaft. In the installed position lower protuberance 130 is held against lateral motion by walls 94, 96, thus preventing rotation of the hemodialyzer.

This initial installation position is the proper operating orientation for the hemodialyzer. Blood flows downhill, coming in port 160, and out port 162; dialysate flows uphill, coming in port 164, and out port 166. Thus, entrapped air in the dialysate side of the hemodialyzer will be expelled by reason of the air naturally rising upward as the dialysate first fills the dialyzer. Entrapped air on the blood side will not be expelled, however, because the blood enters from the top, and rising air will remain in the dialyzer rather than be expelled through the lower blood outlet port. It is necessary to initially turn the dialyzer upside down to degas the blood side of the dialyzer.

The required 180° rotation, as shown in FIG. 5, is accomplished by depressing dialyzer-rotate tab 90, which pivots lower latch element 52 sufficiently away from protuberance 130 to free it from walls 94, 96. Element 52 pivots about the base of vertical leg 92 which rests in wall 100. As it pivots, it forces, by means of bearing surfaces 56 and dowel 54, upper element 50 to pivot in counter rotation, thereby compressing spring 58. The dialyzer is rotated clockwise about axis A'—A' 180° until upper protuberance 132 snaps into place in channel 98 by means of the sloping outer surfaces of walls 94, 96. Counterclockwise rotation is prevented by stop surfaces 152, 154 on base 12. The slope of the outer surfaces of walls 94, 96 provides a force component sufficient to force the lower latch element to rotate, against the resistance of coil spring 58, sufficiently to accept the protuberance. On completion of blood degassing, the hemodialyzer is rotated back to the operating position by following the same steps, beginning with depression of tab 90. During rotation, the bearing surfaces of trunnions 20, 22 cooperate with the bearing surfaces of stub shafts 24, 26, and projections 32, 42 serve to retain axial alignment between these bearing surfaces. In either the operation or inverted position the hemodialyzer is held securely against rotation by two longitudinally spaced connections—the trunnions cooperating with the stub shafts and the protuberance held in the latch.

In addition to permitting rotation for degassing, mount 10 can also be used simply to clamp a fluid flow transfer apparatus in a permanent position by means of the rectangular notch in base 12 between stop surfaces 152 and 154. For example, a hollow fiber dialyzer manufactured by Cobe Laboratories, Inc. does not need to be inverted for degassing, and its generally rectangular casing can be jammed into the above described rectangular notch and held securely therein without the need for arms 14 and 16.

Other embodiments of the invention will be obvious to those skilled in the art.

What is claimed is:

1. A mount for a fluid flow transfer device for facilitating rotation of said device from an upright position to an inverted degassing position, said mount comprising:
   a base;
   two arms rigidly connected to said base for extending adjacent to opposite sides of said device,
   a first bearing surface on each said arm for cooperating with a second bearing surface on each of said opposite sides of said device to permit rotation of said device with respect to said mount about an axis of rotation passing through the rotational centers of said bearing surfaces;
   one of said bearing surfaces being open at its upper surface to receive said other bearing surface when said device is translated radially with respect to said axis of rotation and said device and mount are angularly oriented about said axis in an installation position,
   retention means at said axis of rotation for preventing relative radial translation of said first and second bearing surfaces when said device and mount are angularly oriented in other positions than said installation position, and
   a selectively disengageable first latch on one of said arms, said latch including an axially moveable first latching surface spaced radially from said rotation axis for cooperating with either of a pair of fixed second latching surfaces on said device equally spaced radially from said rotation axis the same distance as said first latching surface is spaced from said axis,
   one of said latching surfaces having a ramp portion inclined with respect to the other said latching surface to move said first latching surface axially away from said device momentarily to allow said latching surfaces to engage,
   whereby said device can be inserted in said mount by translating said device relative to said mount while in said installation orientation such that said first and second bearing surfaces engage, and
   whereby said device, once inserted, can be rotated between operating and degassing positions while retained by first and second bearing surfaces and said retention means, and can be locked into place at each position by engagement of said first and second latching surfaces.

2. The mount of claim 1 wherein said first bearing surfaces are provided by a trunnion on each said arm, said first bearing surface is said one of said bearing surfaces that is open at its upper surface, said second bearing surfaces are provided by a stub shaft on each side of said device, and said second latching surfaces are provided by fixed protuberances extending axially from said device.

3. The mount of claim 2 wherein said stub shafts have hollow interiors and said retention means includes a selectively disengageable second latch in one of said trunnions for preventing removal of said device from said mount, said second latch having a spring biased projection for extending axially inside said interior of at least one said stub shaft, thereby maintaining axial alignment between said trunnions and said stub shafts when said projection is engaged by one of said stub shafts.

4. The mount of claim 3 wherein said projection of said second latch is tapered such that vertically downward insertion of said device causes said projection to snap past said protuberance and the periphery of said stub shaft and come to rest in said interior of said shaft.

5. The mount of claim 2 wherein said first latching surface is formed in part by a latching channel for engaging either of said protuberances, the bottom of said channel being spring biased outward and said ramp portion of said first latching surface being provided by the walls of said channel having outer surfaces that slope down and away from the opening of said channel, whereby said channel walls snap inward past one of said protuberances, thereby engaging said one of said protuberances, when said device is rotated into either said operational position or said inverted degassing position.

6. The mount of claim 5 wherein at least one of said trunnions includes a selectively disengageable, spring biased second latch having a projection for extending axially inside the interior of at least one said stub shaft, thereby maintaining axial alignment between said trunnions and said stub shafts when said projection of said second latch is engaged.

7. The mount of claim 6 wherein said selectively disengageable first latch and one said selectively disengageable second latch are located on the same side of said apparatus and between said first latch and second latch is located a vertical guiding channel for guiding the lower protuberance into said latching channel when said apparatus is inserted downward into said mount during installation.

8. The mount of claim 3 wherein said retention means further includes a fixed projection in the trunnion other than the one with said second latch, said projection being intersected by the trunnion axis and projecting axially inside the interior of said respective stub shaft, and said stub shaft cooperating with said other of said trunnions has a vertically extending radial slot to permit said shaft to be moved downward to position said fixed projection within said interior of said stub shaft.

9. The mount of claim 3 wherein said trunnion having said selectively disengageable second latch has annular lips directed radially inward for engaging with annular lips directed radially outward on said stub shafts, thereby preventing relative axial displacement between said mount and said apparatus.

10. The mount of claim 3 wherein said selectively disengageable second latch further includes a tapered surface on said projection for facilitating installation of said apparatus in said mount and a spring for resisting axial movement of said projection, whereby during installation said projection snaps past the cylindrical exterior of said stub shaft into said hollow interior.

11. The mount of claim 3 wherein said selectively disengageable second latch comprises a second latching element pivoted about a first axis perpendicular to the trunnion axis, said element including said projection, a spring resisting pivoting of said element, and a tab, whereby manual movement of said tab allows said element to pivot sufficiently to withdraw said projection from said hollow interior of said stub shaft, thereby facilitating removal of said apparatus from said mount.

12. The mount of claim 2 wherein said selectively disengageable first latch comprises a first latching element, pivoted about a second axis perpendicular to the trunnion axis and displaced vertically from the installed location of one of said protuberances, and spring means resisting pivoting of said element away from said one of said protuberances, said element including a tab and a pair of walls forming said first latching surface in the shape of a channel, said channel adapted to engage one or the other of said protuberances on said apparatus, whereby movement of said tab pivots said first latch element against said spring sufficiently to disengage said channel from one of said protuberances.

13. The mount of claim 11 wherein the selectively disengageable first latch comprises a first latching element pivoted about a second axis parallel to and below said first axis, said first latching element bearing against said second latching element about said first axis, whereby rotation of said first latching element causes a counter rotation of said second latching element against said spring, thereby providing spring bias for both first and second latches from a single spring.

14. The mount of claim 10 wherein a vertical channel is provided between the trunnion having said selectively disengageable second latch and said selectively disengageable first latch, said channel adapted to guide the lower protuberance on said apparatus into said first latch when said apparatus is inserted into said mount during installation.

15. The mount of claim 3 wherein said selectively disengageable first latch is positioned below said selectively disengageable second latch.

* * * * *